United States Patent [19]
Burd et al.

[11] 4,318,981
[45] Mar. 9, 1982

[54] HOMOGENEOUS SPECIFIC BINDING ASSAY EMPLOYING AN INTRAMOLECULARLY MODULATED PHOTOGENIC ENZYME SUBSTRATE LABEL

[75] Inventors: John F. Burd; Thomas M. Li, both of Elkhart, Ind.

[73] Assignee: Miles Laboratories, Inc., Elkhart, Ind.

[21] Appl. No.: 143,497

[22] Filed: Apr. 24, 1980

[51] Int. Cl.³ ............................................. C12Q 1/66
[52] U.S. Cl. ...................................... 435/7; 23/230 B; 424/12
[58] Field of Search ............................ 435/7; 424/12; 23/230 B

[56] References Cited
U.S. PATENT DOCUMENTS

| 3,880,934 | 4/1975 | Rammler | 435/7 X |
| 3,996,345 | 12/1976 | Ullman et al. | 435/7 X |
| 4,134,792 | 1/1979 | Boguslaski et al. | 435/7 X |
| 4,174,384 | 11/1979 | Ullman et al. | 435/7 X |
| 4,230,797 | 10/1980 | Boguslaski et al. | 435/7 |
| 4,232,119 | 11/1980 | Carlsson et al. | 435/7 |
| 4,238,195 | 12/1980 | Boguslaski et al. | 435/7 X |

Primary Examiner—Robert J. Warden
Attorney, Agent, or Firm—Andrew L. Klawitter

[57] ABSTRACT

A homogeneous specific binding assay method and reagent means for determining a ligand, such as a hapten, antigen or antibody, in, or the ligand binding capacity of, a liquid medium employing a labeled conjugate which upon enzymatic cleavage produces a detectable indicator product. The improvement comprises employing as the label component in the labeled conjugate, a residue having the formula:

$$P-X-M-R$$

wherein P is a photophore, e.g., a fluorescer, which emits light upon exposure to excitation means, X is an enzymatically cleavable linkage, M is a modulator, e.g., a quencher, for said light emission of the photophore, and R is a linking group to the binding component, e.g., the ligand or analog thereof, in the labeled conjugate. The labeled conjugate and the cleaved indicator product emit substantially different amounts of light upon excitation due to modulation of the emission of photophore P by the proximity of modulator M in the labeled conjugate.

40 Claims, 2 Drawing Figures

HOMOGENEOUS SPECIFIC BINDING ASSAY EMPLOYING AN INTRAMOLECULARLY MODULATED PHOTOGENIC ENZYME SUBSTRATE LABEL

BACKGROUND OF THE INVENTION

1. Field of the Invention

The development of specific binding assay techniques has provided extremely useful analytical methods for determining various organic substances of diagnostic, medical, environmental and industrial importance which appear in liquid mediums at very low concentrations. Specific binding assays are based on the specific interaction between the ligand, or analyte under determination, and a binding partner therefor. Where one of the ligand and its binding partner is an antibody and the other is a corresponding hapten or antigen, the assay is known as an immunoassay.

In conventional specific binding assay techniques, a sample of the liquid medium to be assayed is combined with reagent means of various compositions. Such compositions include a labeled conjugate comprising a binding component incorporated with a label. The binding component in the labeled conjugate participates with other constituents, if any, of the reagent means and the ligand in or ligand binding capacity of the medium under assay to form a binding reaction system producing two species or forms of the labeled conjugate, a bound-species and a free-species. In the bound-species, the binding component, e.g., a hapten or antigen, in the labeled conjugate is bound by a corresponding binding partner, e.g., an antibody, whereas in the free-species, the binding component is not so bound. The relative amount or proportion of the labeled conjugate that results in the bound-species compared to the free-species is a function of the presence (or amount) of the ligand or ligand binding capacity to be detected in the test sample.

Where the labeled conjugate in the bound-species is essentially indistinguishable in the presence of the labeled conjugate in the free-species by the means used to monitor the label, the bound-species and the free-species must be physically separated in order to complete the assay. This type of assay is referred to in the art as "heterogeneous". Where the bound-species and free-species forms of the labeled conjugate can be distinguished in the presence of each other, a "homogeneous" format can be followed and the separation step avoided.

This invention relates to assay methods and reagent means of the homogeneous specific binding type of determining qualitatively or quantitatively a ligand in a liquid medium. In particular, the invention relates to an improved homogeneous specific binding assay employing a novel intramolecularly modulated photogenic enzyme substrate as the label component in the labeled conjugate.

2. Description of the Prior Art

The first discovered type of highly sensitive specific binding assay was the radioimmunoassay which employs a radioactive isotope as the label. Such an assay necessarily must follow the heterogeneous format since the monitorable character of the label is qualitatively unchanged in the free- and bound-species. Because of the inconvenience and difficulty of handling radioactive materials and the necessity of a separation step, homogeneous assay systems have been devised using materials other than radioisotopes as the label component, including enzymes, bacteriophages, metals and organometallic complexes, coenzymes, enzyme substrates, enzyme activators and inhibitors, cycling reactants, organic and inorganic catalysts, prosthetic groups, chemiluminescent reactants, and fluorescent molecules.

A homogeneous specific binding assay employing an enzyme-cleavable substrate label is described by Burd et al, *Anal. Biochem.* 77:56(1977) and in German OLS No. 2,618,511 and British Pat. No. 1,552,607 corresponding to U.S. patent application Ser. No. 667,996, filed Mar. 18, 1976, assigned to the present assignee. In exemplified embodiments there is disclosed the use of fluorogenic-labeled conjugates comprising a fluorescer, e.g., umbelliferone or fluorescein, coupled through an enzyme-cleavable bond, e.g., an ester bond, to an appropriate binding component. Cleavage of the linking bond releases the free fluorescer. In forming the labeled conjugate, the fluorescer is coupled at a site which alters its fluoroescence properties. e.g., the fluorescer moiety in the labeled conjugate is essentially nonfluorescent upon exposure to light at the wavelength which causes the enzymatically released fluorescer to fluoresce. In this assay, the rate of fluorescence production, which follows the rate of release of the fluorescer, is a function of the concentration of ligand in the medium under assay.

An improved homogeneous enzyme substrate-labeled specific binding assay is described by Burd et al, *Clin. Chem.* 23:1402(1977) and in U.S. Pat. No. 4,226,978, assigned to the present assignee. The improvement comprises employing as the label component in the labeled conjugate, a residue of the formula:

G—D—R wherein G is a glycone, e.g., β-galactosyl, D is a dye indicator moiety, preferably a fluorescer, e.g., umbelliferone, and R is the linkage to the appropriate binding component. In the presence of a suitable glycosidase enzyme, e.g., β-galactosidase, the glycone moiety is cleaved to release a dye-(binding component) product which is distinct in its fluorescence properties from the labeled conjugate. As in the previously described system, the dye indicator moiety, e.g., fluorescer, is coupled at a site which alters its fluorescence properties. Also, since the fluorescent product of the enzymatic cleavage is a conjugate of the fluorescer and the binding component, performance of the assay is dependent on there being no substantial modulation of the fluorescer by the binding component. Any substantial native modulating character of the binding component could affect the function of the assay.

It is an object of the present invention to provide a homogeneous enzyme substrate-labeled specific binding assay based on a fluorescence detection system, or similar photogenic system (characterized by the production or emission of light), wherein the fluorescer, or photophore, need not be coupled at a critical site in constructing the labeled conjugate, and wherein any native modulating character of the conjugated binding component relative to the photogenicity of the photophore does not affect the function of the assay system.

Of ancillary relevance to the present invention are Weber, *Flavins and Flavoproteins,* ed. Slater, Elsevier (Amsterdam 1966) pp. 15-21; and Forster, *Fluoreszenz organischer Verbindungen,* Vandenhoeck u. Ruprecht (Gottingen 1951) relating to the phenomena of intramolecular collision and energy transfer, and Stryer, Ann.

Rev. Biochem. 47:819 (1978); Yaron et al, Anal. Biochem. 95:228(1979); Ullman et al, J. Biol. Chem. 251:4172(1976); U.S. Pat. No. 3,996,345; British Published Patent Application No. 2,018,424A; and Japanese Laid Open Patent Application No. 53,142,522, relating to the application of the intramolecular energy transfer phenomenon to analytical methods, including enzyme assays and immunoassays.

SUMMARY OF THE INVENTION

The present invention provides a homogeneous specific binding assay method for determining a ligand in, or the ligand binding capacity of, a liquid medium, wherein a liquid reaction mixture is obtained by combining said liquid medium with reagent means including (1) a labeled conjugate having a label component and a binding component, which conjugate is cleavable by an enzyme to produce an indicator product which emits light upon exposure to excitation means, and (2) said enzyme which cleaves said labeled conjugate. In the resulting reaction mixture is formed a binding reaction system having a bound-species and a free-species of the labeled conjugate, the activity of the labeled conjugate as a substrate for the cleaving enzyme being substantially different in the bound-species compared to the free-species. The reaction mixture is thereafter exposed to the excitation means and resulting light emitted is measured as a function of the amount of the ligand in, or the ligand binding capacity of, the liquid medium under assay.

The improvement of the present invention comprises employing as the label component in the labeled conjugate, a residue having the formula:

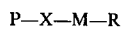

wherein P is a photophore which emits light upon exposure to the excitation means, X is a linkage which is cleavable by the enzyme, M is a modulator for the light emission of photophore P, and R is a linking group through which the label component is covalently bound to the binding component in the labeled conjugate. The labeled conjugate and the cleaved indicator product emit substantially different amounts of light upon exposure to the excitation means due to modulation of the emission of photophore P by the proximity of M in the labeled conjugate.

Photophore P preferably is a fluorescer, and modulator M, preferably a quencher for the fluorescence of P. In such a case, the excitation means is light of a predetermined first wavelength with fluorescer P emitting light at a second, longer, wavelength. Quencher M absorbs the fluorescent emission of P at such second wavelength when proximate to P, as in the labeled conjugate. Thus, the labeled conjugate exhibits substantially less fluorescence at said second wavelength than the cleaved indicator product upon exposure to light of the predetermined first wavelength. Fluorescer P in the cleaved indicator product is substantially unaffected by the presence of quencher M in the surrounding reaction mixture. Where P is a fluorescer and M is a quencher therefor, the amount of ligand in, or the ligand binding capacity of, the liquid medium under assay is related to the resulting light emitted at the second wavelength, or where quencher M is also fluorescent, emitting light at a third, even longer, wavelength, is also related to the resulting light emitted at such third wavelength.

Alternatively, the photophore P can be a chemiluminescer, emitting light upon a chemical reaction, and the modulator M a quencher, absorbing such light emission. Further, as above, such quencher can be a fluorescer, emitting light at a longer wavelength.

The present invention also provides reagent means and labeled conjugates for use in carrying out the improved assay method.

The presently improved assay method and means feature the advantages of not requiring that the photophore be coupled at a site such that the labeled conjugate has different fluorescent properties from the enzymatically cleaved indicator product, and eliminating the possibility that any native modulating character of the conjugated binding component can affect the function of the assay system. In regard to the first advantage, the prior art techniques require careful orientation between the site of attachment to the photophore and the enzymatically cleavable bond such that the labeled conjugate is substantially non-photogenic but release of the photophore upon cleavage produces a photogenic product. In the present invention, the photophore need not be conjugated at a site which affects its photogenic character and the site of attachment need not be adjacent to the enzymatically cleavable bond. These two requirements, which are critical to the prior art techniques, are replaced in the present invention by the single requirement that the modulator be sufficiently proximate to the photophore in the labeled conjugate to modulate its photogenicity.

In regard to the second advantage set forth above, some binding components, e.g., the ligand or analog thereof usually, when incorporated into the labeled conjugate have a native modulating effect, e.g., quenching effect, on the photophore. This property depends on the nature of the binding component and introduces an undesired variable to the design of assays employing such binding components. Also, in the prior art method where the photophore moiety remains attached to the binding component after enzymatic cleavage, the native modulating effect of the binding component continues to affect the photogenicity of the photophore even after enzymatic cleavage of the labeled conjugate. In the present invention, the photophore is cleaved from the binding component and in the labeled conjugate any native modulating character of the binding component is masked by the presence of the modulator. Thus, any such native modulating character is not a factor in the difference in photogenicity expressed by the photophore before and after enzymatic cleavage.

The ultimate advantage in the present invention is that the chemical character of the binding component to be incorporated into the labeled conjugate can be widely varied depending on the ligand or ligand binding capacity of interest without concern for effects on the photogenicity of the photophore before and after enzymatic cleavage. Further, the difference in photogenicity of the photophore before and after cleavage is maximized between a fully modulated state in the labeled conjugate to full expression of photogenicity in the cleaved indicator product. The result is a more universal scheme for preparing labeled conjugates for use in homogeneous enzyme substrate-labeled specific binding assays.

DESCRIPTION OF THE PREFERRED EMBODIMENTS

Figure 1:
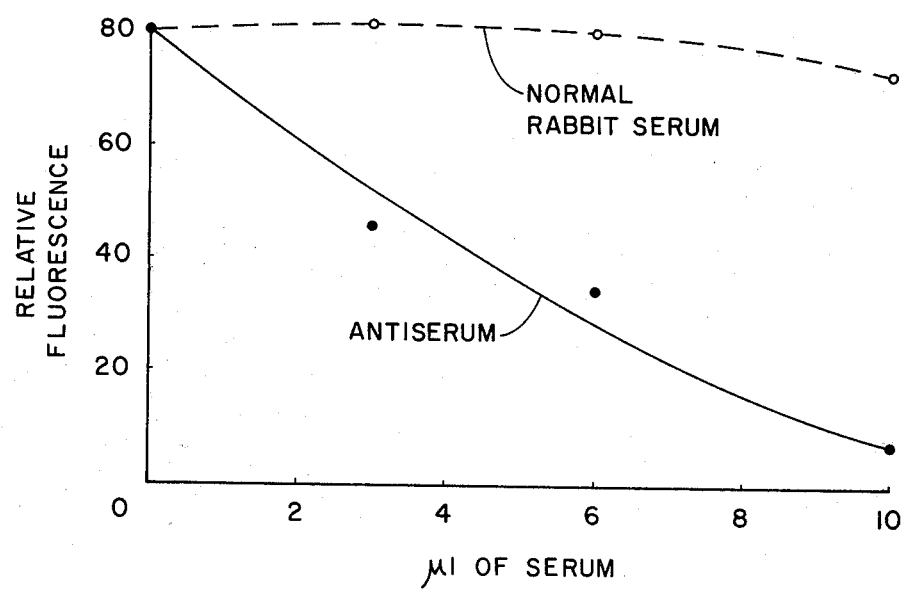
FIG. 1 of the drawing is a typical antibody-binding curve showing the relationship of fluorescence to antibody level in a reaction mixture containing the ligand label conjugate (in this case, a theophylline-FAD conjugate) and cleaving enzyme.

In the context of this disclosure, the following terms shall be defined as follows unless otherwise indicated: "ligand" is the substance, or class of related substances, whose presence, the amount thereof, or the binding capacity therefor in a liquid medium is to be determined; "specific binding partner of the ligand" is any substance, or class of substances, which has a specific binding affinity for the ligand to the exclusion of other substances; "specific binding analog of the ligand" is any substance, or class of substances, which behaves similarly to the ligand with respect to binding by the specific binding partner; and "reagent means" is a composition, device, test kit or other physical arrangement of the reagents used to perform the present assay method.

MODULATION EFFECT

The present invention is based on modulation of the photogenicity, e.g., the ability to emit light upon exposure to excitation means, of the photophore by the proximity of the modulator in the labeled conjugate, and relief of such modulation upon enzymatic cleavage of the linkage between the photophore and modulator. The modulation effect can be based on any physical, chemical or electrical interaction between the photophore and modulator and is usually based on intramolecular modulation, particularly that due essentially to either direct intramolecular collision or resonance energy transfer. Interaction between the photophore and modulator can result either in an increase or decrease in the photogenicity of the photophore. The modulator when proximate to the photophore, as in the labeled conjugate, creates an environment in which the photophore expresses a different photogenicity from that obtained when linkage between the photophore and modulator is cleaved and the photophore is released into the surrounding liquid medium. Where such environment of the labeled conjugate is more favorable to photogenicity, the modulating effect is an increase in photogenicity. Such a situation is found for instance where the photophore is a fluorescer or chemiluminescer which is sensitive to the ionic/nonionic, polar/-nonpolar, or hydrophilic/hydropholic character of its surroundings. Where the modulator induces the environment more favorable to fluorescence or chemiluminescence, the modulating effect is manifested as an enhancement of fluorescence or increase in chemiluminescent emission. For example, various fluorescers are known to exhibit enhanced fluorescence in hydrophobic environments. Such fluorescers include 2-p-toluidinylnaphthalene-6-sulfonate (2,6-TNS); 1-anilinonaphthalene-4-sulfonate(1,4-ANS); 1-anilinonaphthalene-8-sulfonate (1,8-ANS); N-phenyl-1-naphthylamine, and 5-(4'-arsonoanilino)-2-chloro-7-methoxyacridine. Where the modulator has a hydrophobic pocket, the fluorescence of the labeled conjugate will be greater than that of the cleaved fluorescer.

More often, the modulation effect is in the nature of quenching of the photogenicity of the photophore, usually due to direct intramolecular collision or resonance energy transfer.

1. Direct Intramolecular Collision

In this quenching phenomenon, modulation of the photogenicity of the photophore can result from static or dynamic processes. Static quenching results when the photophore and quencher interact prior to excitation of the photophore, whereas dynamic quenching results from interaction with the excited photophore whereby the quenching mechanism competes with emission for depopulation of the excited state. Whereas resonance energy transfer discussed below may take place over a substantially long distance, dynamic and static quenching requires short range collision or contact interaction between the photophore and quencher.

The principles of direct intramolecular collision quenching are described in the literature [Vaughan et al, *Biochem.* 9:464(1970)] and have been applied to analytical chemistry [Guilbault, *Fluorescence, Instrumentation and Practice*, Decker (New York 1967) p. 349], the study of membrane proteins [Shinitzky et al, *Biochem.* 16:982(1977)], the investigation of liposome-cell interactions [Weinstein et al, *Science* 195:489(1977)], and enzyme assays [Yaron et al, *Biochem* 95:228(1979)]. Incorporation of the quencher into the labeled conjugate such that a high frequency of collisions with the photophore is insured provides a system exhibiting direct intramolecular collision quenching.

2. Resonance energy transfer

In this mechanism, energy is transferred from the photophore to a quencher over an intramolecularly long distance, as long as 40 Å but preferably less than 25 Å. The theory of resonance energy transfer has been established by Forster, *Ann. Phys.* 2:55(1948). Unlike direct intramolecular quenching, efficiency of quenching due to resonance energy transfer is dependent upon the spectral overlap of the emission spectrum of the photophore with the absorption spectrum of the quencher. This quenching phenomenon has been applied to enzyme assays [Yaron et al, *Biochem.* 95:228(1970)] and immunoassays [Ullman et al, *J. Biol. Chem.* 251:4172(1976) and U.S. Pat. No. 3,996,345].

PHOTOPHORE/MODULATOR PAIRS

The photophore can be any molecular entity which can be stimulated to emit light by exposure to excitation means of any physical, chemical, or electrical nature, e.g., irradiation with light or exposure to chemical reaction. The principal catagories of the photophore are fluorescers and chemiluminescers. Fluorescers are those molecules which upon irradiation with light of a predetermined first wavelength emit light of a second, longer wavelength. Chemiluminescers emit light upon chemical reaction which may or may not be enzyme catalyzed. When using photophores of either type, modulation of photogenicity is usually through quenching by direct intramolecular collision or resonance energy transfer. Examples of photophore/modulator pairs which can be used in the present invention are provided in the following tables:

| Table No. | Photophore Type | Mode of Quenching |
| --- | --- | --- |
| 1 | Fluorescer | Direct intramolecular collision |
| 2 | Fluorescer | Resonance energy transfer |

-continued

| Table No. | Photophore Type | Mode of Quenching |
|---|---|---|
| 3 | Chemiluminescer | Resonance energy transfer |

TABLE 1

| Fluorescer | Modulator | Reference |
|---|---|---|
| o-aminobenzoate | p-nitrophenyl-alanine | Yaron et al, Anal. Biochem. 95:228(1979) |
| anthracene | p-nitrophenyl-alanine | Yaron et al, Anal. Biochem. 95:228(1979) |
| tryptophan | p-nitrophenyl-alanine | Yaron et al, Anal. Biochem. 95:228(1979) |
| 2-aminoethyl-naphthylamine | p-nitrophenyl-alanine | Yaron et al, Anal. Biochem. 95:228(1979) |
| ethenoadenosine | nicotinamide | Barrio et al, Proc. Nat. Acad. Sci. USA 69:2039(1972) |
| flavin | adenosine | Weber, Biochem. J. 47: 114(1950) |
| flavin | tryptophan | Visser et al, Biochem 16:4883(1977) |
| acridine | adenosine | — |
| tryptophan | MPP[1] | Shinitzky et al, Biochem. 16:982(1977) |
| indole | MPP | Shinitzky et al, Biochem. 16:982(1977) |

[1] N-methyl-4-picolinium perchlorate

TABLE 2

| Fluorescer | Modulator | Reference |
|---|---|---|
| naphthalene | anthracene | Carmel et al, FEBS Letters 30:11(1973) |
| α-naphthylamine | dansyl[2] | Styrer et al, Proc. Nat. Acad. Sci. USA 58: 719(1967) |
| tryptophan | dansyl | Latt et al, Anal. Biochem. 50:56(1972) |
| dansyl | fluorescein | Werner et al, Proc. Nat. Acad. Sci. USA 69:795 (1972) |
| fluorescein | rhodamine | Ullman et al, J. Biol. Chem. 251:4172(1976) |
| tryptophan | fluorescein | Zukin et al, Proc. Nat. Acad. Sci. USA 74:1932 (1972) |
| BPM[3] | thiochrome | Papadakis et al, Biochem. 16: 1890(1977) |
| BPM | ANS[4] | Papadakis et al, Biochem. 16: 1890(1977) |
| thiochrome | DDPM[5] | Papadakis et al, Biochem. 16: 1890(1977) |
| ANS | DDPM | Papadakis et al, Biochem. 16: 1890(1977) |

TABLE 2-continued

| Fluorescer | Modulator | Reference |
|---|---|---|
| | | 1890(1977) |

[2] 5-dimethylamino-1-naphthalenesulfonate
[3] N-[p-(2-benzoxazolyl)phenyl]-maleimide
[4] 8-anilino-1-naphthalenesulfonate
[5] N-(4-dimethylamino-3,5-dinitrophenyl)-maleimide

TABLE 3

| Chemiluminescer | Modulator | Reference |
|---|---|---|
| luminol | fluorescein | Rusin et al, Khim. Vys. Energ. 10:92(1976) |
| " | eosin | Rusin et al, Khim. Vys. Energ. 10:92(1976) |
| " | rhodamine S | Rusin et al, Khim. Vys. Energ. 10:92(1976) |
| DBPD[6] | 9,10-diphenyl-anthracene | Roswell et al, J.A.C.S. 92: 4855(1970) |
| DBD[7] | N-methylacri-done | Roberts et al, J.A.C.S. 92: 4861(1970) |
| " | carbazole | Roberts et al, J.A.C.S. 92: 4861(1970) |
| " | 2,3-benzocar-bazole | Roberts et al, J.A.C.S. 92: 4861(1970) |
| " | 3,4-benzocar-bazole | Roberts et al, J.A.C.S. 92: 4861(1970) |

[6] 2,3-dihydrobenzo[g]phthalazine-1,4-dione
[7] 2,3-dihydrophthalazine-1,4-dione Following are exemplary structures of some fluorescer/modulator labeled conjugates contemplated for use in the present invention:

A. Flavin/adenosine labeled conjugate

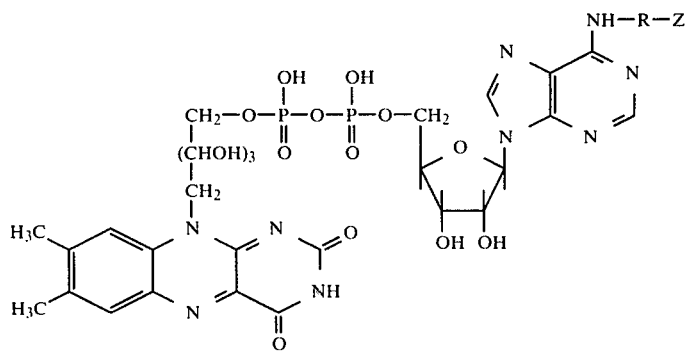

wherein R is the linking group as defined herein and Z is the binding component as defined herein. The flavin portion of the conjugate is the fluorescer whose fluorescence is quenched by direct intramolecular collision with the adenosine moiety. The conjugate is appropriately cleaved by a nucleotide pyrophosphatase enzyme to relieve quenching. Reference: Weber, Biochem. J. 47:114(1950).

B. Ethenoadenosine/nicotinamide labeled conjugate

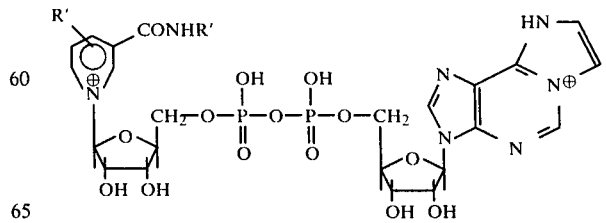

wherein one of R' is —R—Z as above and the other is hydrogen. The ethenoadenosine portion of the conjugate is the fluorescer whose fluoresence is quenched by direct intramolecular collision with the nicotinamide moiety. The conjugate is appropriately cleaved by an NADase or phosphodiesterase enzyme to relieve quenching. Reference: Barrio et al, *Proc. Nat. Acad. Sci USA* 69:2039(1972).

C. Fluorescer/p-nitrobenzyl labeled conjugates

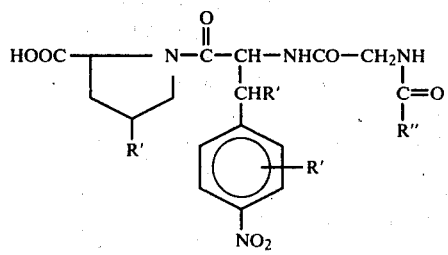

wherein one of R' is —R—Z as above and the others are hydrogen, and R" is one of the following

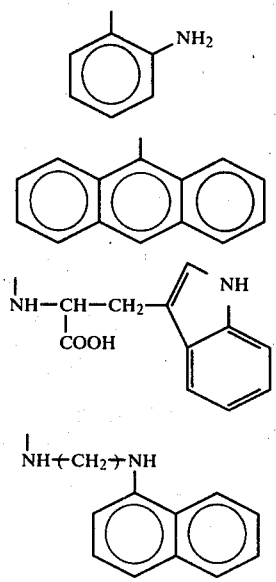

The moieties (a)-(d) of the conjugate are the fluorescers whose fluorescence is quenched by direct intramolecular collision with the p-nitrobenzyl portion. The conjugate is appropriately cleaved by angiotensin-1-converting enzyme. Reference: Carmel et al, *Clin. Chem. Acta* 93:215(1979)

D. o-Aminobenzoate/p-nitrobenzyl labeled conjugates

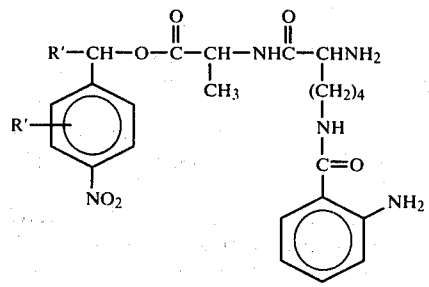

wherein one of R' is —R—Z as above and the other is hydrogen. The o-aminobenzoate portion of the conjugate is the fluorescer whose fluorescence is quenched by direct intramolecular collision with the p-nitrobenzyl moiety. The conjugate is appropriately cleaved by leucine aminopeptidase enzyme. Reference: Carmel et al, *Eur. J. Biochem.* 73:617(1977).

E. Naphthalene/anthracene labeled conjugate

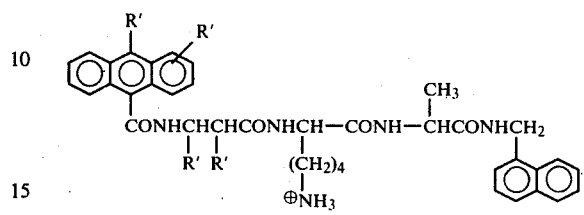

wherein one of R' is —R—Z as above and the others are hydrogen. The naphthyl portion of the conjugate is the fluorescer whose fluorescence is quenched by resonance energy transfer with the anthracene moiety. The conjugate is appropriately cleaved by trypsin. Reference: Carmel et al, *FEBS Letters* 30:11(1973).

F. Tryptophan/dansyl labeled conjugate

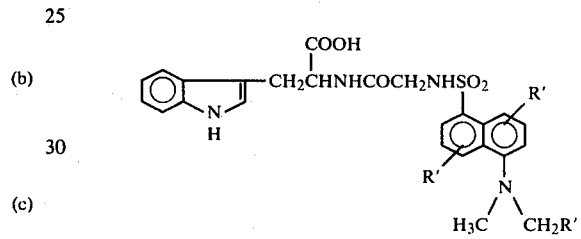

wherein one of R' is —R—Z as above and the others are hydrogen. The tryptophan portion of the conjugate is the fluorescer whose fluorescence is quenched by resonance energy transfer with the dansyl moiety. The conjugate is appropriately cleaved by carboxypeptidase A. Reference: Latt et al, *Anal. Biochem.* 50:56(1972).

Where the modulator is also a fluorescer, it is possible to monitor the specific binding reaction by measuring either the photogenicity of the photophore or the fluorescence of the modulator. For instance, where the photophore is a fluorescer or a chemiluminescer and the emission therefrom is of a wavelength to excite the fluorescent modulator, e.g., a fluorescent quencher, one can monitor either the photophore emission or the fluorescent modulator emission.

ENZYME CLEAVABLE LINKAGE

In the labeled conjugate of the present invention, the photophore and modulator are chemically linked by a chain comprising an enzyme cleavable bond. The length of the chain and its chemical nature are limited only in so far that the modulator is sufficiently proximate to the photophore to have its desired modulating effect. In one preferred aspect, where the photophore is a fluorescer and the modulator a quencher by direct intramolecular collision, the linking chain therebetween must be sufficiently flexible and/or conformationally oriented to promote the desired collision or contact between fluorescer and quencher. On the other hand, where quenching is due to resonance energy transfer, the only requirement is that the distance between photophore and quencher be maintained within prescribed tolerances for effective energy transfer. Thus, depending on the specific photophore and modulator involved, the chain therebetween may consist of the enzyme cleavable bond alone or, as is most often the case, may comprise a linkage which includes at some appropriate point along its length the enzymatically cleavable bond. Thus, as described herein, the enzyme cleavable linkage is the chain between the photophore and modulator and containing the enzyme cleavable bond. Examples of such enzyme cleavable bonds are ester bonds, cleavable by esterases, particularly phosphoric diester bonds cleavable by phosphodiesterase; glycosyl bonds, cleavable by glycoside hydrolases, e.g., amylases; and peptide bonds, cleavable by peptidases such as leucine aminopeptidase, carboxypeptidase A, pepsin, trypsin, chymotrypsin, papain, and thrombin.

The enzymatically cleavable linkage will be attached to the photophore and modulator respectively such that the photogenic and modulating characters thereof are preserved at least to a degree that a binding assay can be performed. The photophore will normally be coupled at a site which is inert relative to its photogenic character. For example, where the photophore is a fluorescer, it will be derivatized or coupled at a position other than one which when chemically modified results in substantial changes in the spectral properties of the fluorescer. In the usual case, the majority of available coupling sites on the fluorescer will have such a noncritical character, permitting selection from a wide variety of coupling sites and routes in designing labeled conjugates of the present invention.

LINKING GROUP/BINDING COMPONENT

The particular choice of binding component in the labeled conjugate will depend on the homogeneous assay technique selected as described in detail hereinafter, however, it will usually comprise the ligand to be determined, a binding analog thereof (e.g., a derivative of the ligand or synthetic precursor of the ligand), or a binding partner thereof. Selection of the binding component for a particular assay and the means for incorporating same into the labeled conjugate are matters of ordinary skill in the art. In choosing the sites of attachment to the binding component and the modulator, the important considerations are (1) preservation of the ability of the linked binding component to participate effectively in the selected binding assay system and (2) preservation of the ability of the linked modulator to modulate the photogenic character of the conjugated photophore, in both cases, to the extent that a useful assay will result for the particular ligand or ligand binding capacity under assay and for the particular concentrations or amounts in which such is to be detected. Usually, the linking group will comprise a chemical bond, usually a single, but sometimes a double bond, or a chain containing between 1 to 20, more commonly 1 to 10, carbon atoms and 0 to 10, more commonly 1 to 5, heteroatoms selected from nitrogen, oxygen, and sulfur. Further details regarding the selection of linking groups may be found in British Published patent application No. 2,023,607A corresponding to U.S. patent application Ser. No. 917,961, filed June 22, 1978, assigned to the present assignee, and in U.S. Pat. No. 3,817,837.

LIGAND

The present assay may be applied to the detection of any ligand for which there is a specific binding partner and, conversely, to the detection of the capacity of a liquid medium to bond a ligand (usually due to the presence of a binding partner for the ligand in the medium). The ligand usually is a peptide, polypeptide, protein, carbohydrate, glycoprotein, steroid, or other organic molecule for which a specific binding partner exists in biological systems or can be synthesized. The ligand, in functional terms, is usually selected from the group comprising antigens and antibodies thereto; haptens and antibodies thereto; and hormones, vitamins, metabolites and pharmacological agents, and their receptors and binding substances. Usually, the ligand is an immunologically-active polypeptide or protein of molecular weight between 1,000 and 10,000,000, such as an antibody or antigenic polypeptide or protein, or a hapten of molecular weight between 100 and 1,500.

Representative polypeptide ligands are angiotensin I and II, C-peptide, oxytocin, vasopressin, neurophysin, gastrin, secretin, bradykinnin, and glucagon.

Representative protein ligands include the classes of protamines, mucoproteins, glycoproteins, globulins, albumins, scleroproteins, phosphoproteins, histones, lipoproteins, chromoproteins, and nucleoproteins. Examples of specific proteins are prealbumin, $\alpha_1$-lipoprotein, human serum albumin, $\alpha_1$-acid glycoprotein, $\alpha_1$-antitrypsin, $\alpha_1$-glycoprotein, transcortin, thyroxine binding globulin, haptoglobin, hemoglobin, myoglobin, ceruloplasmin, $\alpha_2$-lipoprotein, $\alpha_2$-macroglobulin, $\beta$-lipoprotein, erythropoietin, transferin, homopexin, fibrinogen, the immunoglobulins such as IgG, IgM, IgA, IgD, and IgE, and their fragments, e.g., $F_c$ and $F_{ab}$, complement factors, prolactin, blood clotting factors such as fibrinogen, thrombin and so forth, insulin, melanotropin, somatotropin, thyrotropin, follicle stimulating hormone, leutinizing hormone, gonadotropin, thyroid stimulating hormone, placental lactogen, intrinsic factor, transcobalamin, serum enzymes such as alkaline phosphatase, lactic dehydrogenase, amylase, lipase, phosphatases, cholinesterase, glutamic oxaloacetic transaminase, glutamic pyruvic transaminase, and uropepsin, endorphins, enkephalins, protamine, tissue antigens, bacterial antigens, and viral antigens such as hepatitis associated antigens (e.g., $HB_sAg$, $HB_cAg$ and $HB_eAg$).

Representative hapten ligands include the general classes of drugs, metabolites, hormones, vitamins, and the like organic compounds. Haptenic hormones include thyroxine and triiodothyronine. Vitamins include vitamins A, B, e.g., $B_{12}$, C, D, E and K, folic acid and thiamine. Drugs include antibiotics such as aminoglycosides, e.g., gentamicin, tobramycin, amikacin, sisomicin, kanamycin, and netilmicin, penicillin, tetracycline, terramycin, chloromycetin, and antinomycetin; nucleosides and nucleotides such as adenosine diphosphate (ADP) adenosine triphosphate (ATP), flavin mononucleotide (FMN), nicotinamide adenine dinucleotide (NAD) and its phosphate derivative (NADP), thymidine, guanosine and adenosine; prostaglandins; steroids such as the estrogens, e.g., estriol and estradiol, sterogens, androgens, digoxin, digitoxin, and adrenocortical steroids; and others such as phenobarbital, phenytoin, primidone, ethosuximide, carbamazepine, valproate, theophylline, caffeine, propranolol, procainamide, quinidine, amitryptiline, cortisol, desipramine, disopyramide, doxepin, doxorubicin, nortryptiline, methotrexate, imipramine, lidocaine, procainamide, N-acetylprocainamide, amphetamines, catecholamines, and antihistamines.

HOMOGENEOUS ASSAY TECHNIQUES

In the homogeneous assay technique, i.e., an assay technique which does not require a physical separation of the bound-species and the free-species, reaction between the binding component in the labeled conjugate and a corresponding binding partner causes a measurable change, either in a positive or a negative sense, in the light emitted upon exposure of the reaction mixture to excitation means as described herein. The distribution of the labeled conjugate between the bound-species and the free-species is differentiated by the inability or altered ability of the enzyme to cleave such conjugate when in the bound-species, and thus the inability or altered ability of the enzyme to relieve modulation of the conjugated photophore. Several manipulative techniques are available for carrying out a homogeneous assay with the most common technique being the competitive binding technique. In the competitive binding technique, the liquid medium is contacted with a specific binding partner of the ligand, a labeled conjugate comprising the photophore/modulator label coupled to the ligand or a specific binding analog thereof, and the cleaving enzyme, and thereafter a resulting light emission upon exposure to excitation means is assessed.

Determination of the ligand binding capacity of, e.g., the presence of a specific binding partner of the ligand in, a liquid medium can be accomplished by a homogeneous technique by contacting the liquid medium with a conjugate comprising the photophore/modulator label coupled to the ligand or a specific binding analog thereof, and with the cleaving enzyme, and measuring a resulting light emission.

In general, when following the homogeneous assay technique, the components of the assay reaction, i.e., the liquid medium suspected of containing the ligand, the labeled conjugate, the cleaving enzyme, and, if necessary, a specific binding partner of the ligand, may be combined in any amount, manner, and sequence, provided that a resulting light emission upon exposure to the excitation means is measurably altered when the liquid medium contains the ligand in an amount or concentration of significance to the purposes of the assay. Preferably, all of the components of the specific binding reaction are soluble in the liquid medium.

It is contemplated that manipulative schemes involving other orders of addition and other binding reaction formats can be devised for carrying out homogeneous specific binding assays without departing from the inventive concept embodied herein.

The liquid medium to be assayed can be a naturally occurring or artificially formed liquid suspected to contain the ligand, and usually is a biological fluid or a dilution thereof. Biological fluids that can be assayed include serum, plasma, urine, saliva, and amniotic and cerebrospinal fluid.

The binding reaction will in almost all cases be allowed to proceed under mild conditions. The reaction mixture will be in general an aqueous medium with any desirable organic cosolvents being present in minor amounts. The temperature of the reaction will be maintained at a constant level in normal circumstances throughout the incubation period and the measurement step. Temperatures will generally be between 5° and 50° C., more usually between 20° and 40° C. Preferably the reaction will proceed at room temperature. The pH of the reaction mixture will vary between 5 and 10, more usually between 6 and 9. The concentration of the various reagents will depend on the level of ligand or ligand binding capacity expected in the test medium, with such level usually being between $10^{-3}$ and $10^{-12}$ M. As in the case of the previously described reaction parameters, selection is primarily based on empirically derived optimization balanced against the preferences and needs of the technician who will ultimately perform assays on a routine basis. None of the parameters therefor are of a critical nature to the present invention, rather they are all within the ordinary skill in the art.

REAGENT MEANS

The reagent means of the present invention comprises all of the essential chemical elements required to conduct a desired assay method encompassed by the present invention. The reagent means is presented in a commercially packaged form, as a composition or admixture where the compatability of the reagents will allow, in a test device configuration, or as a test kit, i.e., a packaged combination of one or more containers holding the necessary reagents. Included in the reagent means are the reagents appropriate for the binding reaction system desired, always requiring a labeled conjugate as defined hereinbefore. Such binding reaction reagents can include, in addition to the labeled conjugate, a binding partner to the ligand and so forth. Of course, the reagent means can include other reagents as are known in the art and which may be desirable from a commercial and user standpoint, such as buffers, diluents, standards, and so forth.

The present invention will now be illustrated, but is not intended to be limited, by the following example of a homogeneous immunoassay for determining the therapeutic drug theophylline in serum. In the exemplified assay, the label component of the labeled conjugate has the formula:

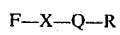

wherein F is a fluorescer moiety, X is an enzymatically cleavable linkage, Q is a quencher moiety, and R is the linkage to the binding component. In the example, the residue F—X—Q— is flavin adenine dinucleotide (FAD) coupled at the $N^6$ position of its adenine moiety through linking group R to a derivative of theophylline. The flavin portion of FAD serves as the fluorescer, the adenosine moiety of FAD serves as the quencher, and the pyrophosphate linking group in FAD is comprised in the enzyme cleavable linkage. The native fluorescence of flavin is effectively quenched by intramolecular contact with the adenine ring in the adenosine moiety of FAD. Cleavage of the pyrophosphate linkage by nucleotide pyrophosphatase releases the fluorescent product flavin mononucleotide (FMN). The fluorescence of FAD is approximately 10 percent of that of FMN.

Preparation of the Labeled Conjugate

Preparation of the FAD-theophylline conjugate proceeded as follows. $N^6$-Trifluoroacetamidohexyl-adenosine-5'-monophosphate was synthesized by reacting 6-chloropurineriboside-5'-monophosphate with 1,6-hexanediamine according to the method of Trayer et al, Biochem. J. 139:609(1974), followed by blocking the terminal amino group with a trifluoroacetyl group.

Fifty-six milligrams (mg) [0.1 millimole (mmol)] of $N^6$-trifluoroacetamidohexyl-adenosine-5'-monophosphate was dissolved in about 10 milliliters (ml) of water and 25 microliters (μl) of tri-n-butylamine (0.1 mmol)

was added. The water was removed under vacuum and the residue was dissolved in 10 ml of dry dimethyl formamide (DMF) which was then removed under vacuum. The residue was evaporated from dry DMF three more times. The final residue was dissolved in 10 ml of dry DMF. Eightly milligrams of N,N'-carbonyldiimidazole (0.4 mmol) was added and allowed to react for 1.5 hours. Then 15 μl of water was added and the solvent was removed under vacuum. The residue, $N^6$-trifluoroacetamidohexyl-adenosine-5'-monophosphate imidazolide, was dissolved in 10 ml of DMF.

Forty-seven milligrams of riboflavin-5'-monophosphate (0.1 mmol), prepared as described by Johnson et al, *Anal. Biochem.* 86:526(1978), was dissolved in about 10 ml of water and added dropwise to 20 ml of acetone containing 43 μl of tri-n-octylamine (0.1 mmol). A precipitate formed before the addition was complete. The solvent was removed with a rotary evaporator until the riboflavin-5'-monophosphate dissolved. Then 5 ml of acetone and 5–10 ml of DMF were added and the mixture was taken to dryness. The residue was dissolved in 15–20 ml of dry DMF and taken to dryness (this process was repeated three times). The residue was dissolved in 5 ml of dry DMF and combined with the above-mentioned 10 ml solution of the imidazolide in dry DMF.

The reaction mixture was allowed to stand at room temperature overnight and then the solvent was removed. The residue was taken up in 50 ml of water and applied to a 2.5×25 centimeter (cm) column of DEAE-cellulose in the bicarbonate form (Whatman DE23, Reeve Angel, Clifton, N.J.). The chromatogram was developed with a linear gradient generated with two liters of water and two liters of 0.3 molar (M) ammonium bicarbonate (23 ml fractions were collected). Thin-layer chromatography on silica gel 60 F254 (E. Merck, Darmstadt, West Germany) using a 7:3 volume:volume (v:v) mixture of ethanol-1 M triethylammonium bicarbonate (pH 7.5) showed that fractions numbered 68 to 73 contained major ($R_f=0.75$) and minor ($R_f=0.36$) yellow components. These fractions were pooled and the optical absorption spectrum had maxima at 267, 373 and 450 nanometers (nm).

The solvent was removed from the pooled material and the residue was dissolved in about 5 ml of water. This solution was adjusted to pH 11.0 with 5 N sodium hydroxide and allowed to stand at room temperature for nine hours. Thin-layer chromatography showed that the component with $R_f=0.75$ disappeared while a new yellow material with $R_f=0.37$ appeared. The latter material gave a positive reaction with ninhydrin. Some yellow material with $R_f=0.75$ was not changed by the alkaline conditions and was probably riboflavin cyclic-4',5'-monophosphate.

The reaction mixture was adjusted to pH 8.0 with hydrochloric acid and applied to a 2.5×20 cm column of DEAE-cellulose in the bicarbonate form. The chromatogram was developed with a linear gradient developed with one liter of water and one liter of 0.2 M ammonium bicarbonate. Separation of the major yellow components was not achieved. The yellow effluent from the column was pooled and the solvent was removed. The residue was adsorbed onto 2 grams (g) of silica gel which was placed atop a 50 g column of silica gel equilibrated with a 9:2 (v:v) mixture of ethanol-1 M triethylammonium bicarbonate (pH 7.5). When the column was washed with this same solvent mixture, the yellow component with $R_f=0.75$ eluted with considerable tailing. The solvent ratio was changed to 8:2 and the yellow component with $R_f=0.37$ eluted along with some of the material with $R_f=0.75$. The yellow effluent containing the component with $R_f=0.37$ was collected and the solvent was removed. The yield of flavin $N^6$-(6-aminohexyl)-adenine dinucleotide based on absorbance at 450 nm was about 10%.

This material had optical absorption maxima at 265, 373, and 450 nm. A sample was spotted on a thin-layer chromatography plate which was developed with ethanol-1 M triethylamminium bicarbonate, pH 7.5 (7:3). The yellow bands were scraped from the plate and the yellow compounds were each eluted from the silica gel with water. Absorbance measurements at 450 nm indicated that the components with $R_f=0.37$ and 0.75 represented 70% and 30%, respectively, of the flavins in the mixture. A sample of the mixture was dissolved in 0.1 M tris-(hydroxymethyl)-aminomethane-hydrochloride buffer, pH 8.5, and allowed to react overnight with a snake venom phosphodiesterase preparation (*Croteus adamatous*) obtained from Worthington Biochemicals, Freehold, N.J. The material with $R_f=0.37$ was completely hydrolyzed to FMN while the material with $R_f=0.75$ was not affected. In a control reaction, the snake venom preparation hydrolyzed FAD to FMN.

To a solution of 2.4 μmol flavin $N^6$-(6-aminohexyl)-adenine dinucleotide, prepared as described above, in 200 μl dimethylsulfoxide under argon gas was added 0.9 mg (3.62 μmol) 1,3-dimethyl-1,6,7,8-tetrahydropyrido[1,2-3]purine-2,4,9(3H)-trione, prepared according to the method of Cook, et al, *Res. Commun. Chem. Path. and Pharmacol.* 13:497(1976), followed after 4 hours by addition of a further 1.8 mg (7.3 μmol) of the same (trione). After stirring overnight, the solvent was evaporated under vacuum (0.1 mm Hg) and the residue chromatographed on a 2.5×90 cm LH-20 Sephadex (Pharmacia Fine Chemicals, Uppsala, Sweden) column equilibrated and eluted with 0.3 M triethylammonium bicarbonate buffer (pH 7.8). The crude product eluting between 216 and 246 ml of the effluent was collected, applied to a 20×20 cm×1000μ silica gel plate and chromatographed using an 8:2 ethanol: 1 M triethylammonium bicarbonate buffer (pH 7.8) mixture. The band containing the desired product ($R_f=0.77$) was scraped from the plate, extracted with 1 M triethylammonium bicarbonate buffer (pH 7.8), filtered and concentrated. Final purification by chromatography on LH-20 Sephadex equilibrated and eluted with the buffer at 0.3 M gave 1.26 μmoles of the FAD-theophylline labeled conjugate as determined by absorbance measurement at 450 nm, which was a yield of 53%.

Assay Reagents

FAD-theophylline solution—The FAD-theophylline conjugate dissolved in 50 mM Bicine buffer [N,N-bis-(2-hydroxyethyl)-glycine from Calbiochem, La Jolla, Calif.], pH 8.5.

Antiserum to theophylline—Raised in rabbits immunized with a theophylline-BSA immunogen prepared by coupling 8-(3-carboxypropyl) theophylline to BSA, Cook et al, *Res. Commun. Chem. Path. Pharmacol.* 13:497(1976).

Nucleotide pyrophosphatase—Snake venom enzyme obtained from Sigma Chemical Co., St. Louis, Mo.

Assay Method

Antibody-binding curves were obtained by preparing reaction mixtures in cuvettes by adding varying levels of antiserum to theophylline or normal rabbit serum to 2.0 ml Bicine buffer, pH 8.5, containing 50 nM FAD-theophylline. At timed intervals, 0.16 units of nucleotide pyrophosphatase was added and mixed. The fluorescence intensity was measured in each cuvette 20 minutes after the enzyme addition. The fluorescence of cuvettes containing all reaction components except enzyme was subtracted from the appropriate reaction cuvettes. A typical antibody-binding curve is depicted in FIG. 1 of the drawing.

Figure 2:
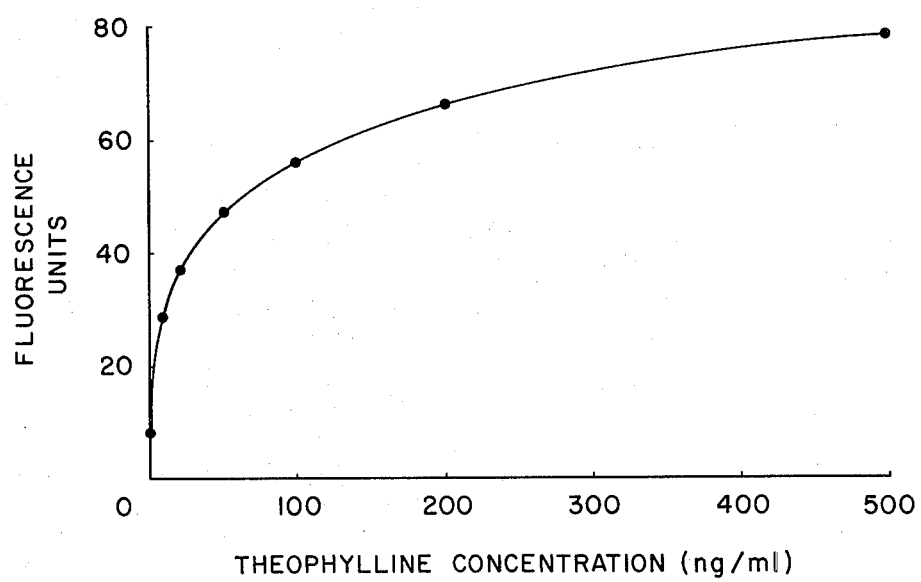
FIG. 2 of the drawing is a typical standard curve for use in an assay to determine the concentration of a ligand (in this case, theophylline) in a liquid medium.

Competitive binding reaction mixtures were prepared in cuvettes to contain 2.0 ml Bicine buffer, pH 8.5, 8 μl antiserum to theophylline, 20 μl snake venom nucleotide pyrophosphate and theophylline at predetermined levels. At 20 second intervals, 100 μl of 1.0μ molar FAD-theophylline was added to the cuvettes in series and the contents mixed. The fluorescence of released FMN was measured in each cuvette 20 minutes after addition of the enzyme with an Aminco-Bowman spectrophotofluorometer at room temperature, excitation—445 nm and emission—525 nm. Fluorescence was recorded in arbitrary fluorescence units from the instrument reading. A typical curve relating theophylline concentration in the 2 ml reaction volume to fluorescence intensity is depicted in FIG. 2 of the drawing.

What is claimed is:

1. In a homogeneous specific binding assay method for determining a ligand in, or the ligand binding capacity of, a liquid medium, wherein a liquid reaction mixture is obtained by combining said liquid medium with reagent means including (1) a labeled conjugate having a label component and a binding component, which conjugate is cleavable by an enzyme to produce an indicator product which emits light upon exposure to excitation means, and (2) said enzyme which cleaves said labeled conjugate, thereby forming in said reaction mixture a binding reaction system having a bound-species and a free-species of said labeled conjugate, the activity of said labeled conjugate as a substrate for said cleaving enzyme being substantially different in said bound-species compared to said free-species, and wherein said reaction mixture is exposed to said excitation means and resulting light emitted is measured as a function of the amount of said ligand in, or said ligand binding capacity of, said liquid medium, the improvement which comprises employing as said label component of said labeled conjugate, a residue having the formula:

P—X—M—R wherein P is a photophore which emits light upon exposure to said excitation means, X is a linkage which is cleavable by said enzyme, M is a modulator for said light emission of said photophore, and R is a linking group through which said label component is covalently bound to the binding component in said conjugate, said labeled conjugate and said cleaved indicator product emitting substantially different amounts of light upon exposure to said excitation means due to modulation of the emission of P by the proximity of M in said labeled conjugate.

2. The method of claim 1 wherein P is a fluorescer.

3. The method of claim 2 wherein said excitation means is light of a predetermined first wavelength, said fluorescer P emitting light at a second wavelength, and wherein M is a quencher which absorbs the fluorescent emission of P at said second wavelength, said labeled conjugate exhibiting substantially less fluorescence of said second wavelength than said cleaved indicator product upon exposure to light of said predetermined first wavelength due to quenching of the fluorescence of P by the proximity of M in said labeled conjugate.

4. The method of claim 3 wherein quenching of the fluorescence of P by M is due essentially to direct intramolecular collision and wherein said fluorescer P comprises a residue of flavin, anthracene, tryptophan, o-aminobenzoic acid, 2-aminoethylnaphthylamine, ethenoadenosine, acridine, or indole.

5. The method of claim 3 wherein quenching of the fluorescence of P by M is due essentially to resonance energy transfer and wherein said fluorescer P comprises a residue of naphthalene, tryptophan, fluorescein, thiochrome, N-[p-(2-benzoxazolyl)phenyl]-maleimide, or N-(4-dimethylamino-3,5-dinitrophenyl)-maleimide.

6. The method of claim 3 wherein said label component is flavin adenine dinucleotide (FAD) coupled through the adenine moiety by the linking group R to said binding component of the labeled conjugate, the flavin portion of FAD serving as said fluorescer, the adenosine moiety of FAD serving as said quencher, and the pyrophosphate linking group in FAD serving as said enzyme cleavable linkage, and wherein said enzyme is nucleotide pyrophosphatase.

7. The method of claim 6 wherein FAD is coupled at the $N^6$ position of the adenine moiety to the linking group R.

8. The method of claim 3 wherein said reaction mixture is irradiated with light of said predetermined first wavelength and the resulting light emitted at said second wavelength is measured as a function of the amount of said ligand in, or the ligand binding capacity of, said liquid medium.

9. The method of claim 3 wherein said quencher M is a fluorescer which emits light at a third wavelength, and wherein said reaction mixture is irradiated with light of said predetermined first wavelength and the resulting light emitted at said third wavelength is measured as a function of the amount of said ligand in, or the ligand binding capacity of, said liquid medium.

10. The method of claim 1 wherein P is a chemiluminescer and M is a quencher which absorbs the emission of P, and wherein said excitation means comprises chemical reagents which react with said chemiluminescer to cause same to emit light, said labeled conjugate emitting substantially less light than said detectable indicator product upon exposure to said chemical reagents due to quenching of the chemiluminescence of P by the proximity of M in said labeled conjugate.

11. The method of claim 10 wherein the resulting light emitted by chemiluminescer P is measured as a function of the amount of said ligand in, or the ligand binding capacity of, said liquid medium.

12. The method of claim 10 wherein said quencher M is a fluorescer which emits light at a wavelength different from the emission of chemiluminescer P and wherein the resulting light emitted at said different wavelength is measured as a function of the amount of said ligand in, or the ligand binding capacity of, said liquid medium.

13. The method of claim 1 wherein said ligand is selected from the group consisting of antigens and antibodies thereto; haptens and antibodies thereto; and hormones, vitamins, metabolites, and pharmacological agents, and their receptors and binding substances.

14. In a homogeneous specific binding assay method for determining a ligand in a liquid medium, or for determining the ligand binding capacity of a liquid medium suspected to contain a specific binding partner of said ligand,
wherein a liquid reaction mixture is obtained by combining said liquid medium with
(1) a labeled conjugate having a label component coupled to said ligand or a binding analog thereof, which conjugate is cleavable by an enzyme to produce an indicator product which fluoresces upon excitation with light of a predetermined first wavelength, emitting light at a second wavelength,
(2) said enzyme which cleaves said labeled conjugate, and,
(3) where said ligand is under determination, a specific binding partner of said ligand, and
the activity of said labeled conjugate as a substrate for said cleaving enzyme being substantially decreased by binding of said specific binding partner, and
wherein said reaction mixture is irradiated with light of said predetermined first wavelength and resulting fluorescence is measured as a function of the amount of said ligand in, or said ligand binding capacity of, said liquid medium,
the improvement which comprises employing as said label component of said labeled conjugate, a residue having the formula:

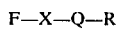

F—X—Q—R wherein F is a fluorescer which is excited by light of said predetermined first wavelength to emit light at said second wavelength, X is a linkage which is cleavable by said enzyme, Q is a quencher which when proximal to fluorescer F absorbs the fluorescent emission of fluorescer F at said second wavelength, and R is a linking group through which said label component is covalently bound to said ligand or analog thereof in said conjugate, said labeled conjugate exhibiting substantially less fluorescence at said second wavelength than said cleaved indicator product upon irradiation with light of said predetermined first wavelength due to quenching of the fluorescence of F by proximity of Q in said labeled conjugate.

15. The method of claim 14 wherein quenching of the fluorescence of F by Q is due essentially to direct intramolecular collision and wherein said fluorescer F comprises a residue of flavin, anthracene, tryptophan, o-aminobenzoic acid, 2-aminoethylnaphthylamine, ethenoadenosine, acridine, or indole.

16. The method of claim 14 wherein quenching of the fluorescence of F by Q is due essentially to resonance energy transfer and wherein said fluorescer F comprises a residue of naphthalene, tryptophan, fluorescein, thiochrome, N-[p-(2-benzoxazoyl)phenyl]-maleimide, or N-(4-dimethylamine-3,5-dinitrophenyl)-maleimide.

17. The method of claim 14 wherein said label component is flavin adenine dinucleotide (FAD) coupled through the adenine moiety by the linking group R to said binding component of the labeled conjugate, the flavin portion of FAD serving as said fluorescer, the adenosine moiety of FAD serving as said quencher, and the pyrophosphate linking group in FAD serving as said enzyme cleavable linkage, and wherein said enzyme is nucleotide pyrophosphatase.

18. The method of claim 17 wherein FAD is coupled at the $N^6$ position of the adenine moiety to the linking group R.

19. The method of claim 14 wherein said reaction mixture is irradiated with light of said predetermined first wavelength and the resulting light emitted at said second wavelength is measured as a function of the amount of said ligand in said liquid medium.

20. The method of claim 14 wherein said ligand is selected from the group consisting of antigens and antibodies thereto; haptens and antibodies thereto; and hormones, vitamins, metabolites, and pharmacological agents, and their receptors and binding substances.

21. The method of claim 14 wherein said ligand is an antigenic polypeptide or protein or a hapten having a molecular weight of at least 100.

22. The method of claim 14 wherein said ligand is a hapten having a molecular weight of between 100 and 1500.

23. In a reagent means for use in a homogeneous specific binding assay method for determining a ligand in, or the ligand binding capacity of, a liquid medium, which means comprises
(1) a labeled conjugate having a label component and a binding component, which conjugate is cleavable by an enzyme to produce an indicator product which emits light upon exposure to excitation means, and
(2) said enzyme which cleaves said labeled conjugate,
the improvement wherein said label component of said labeled conjugate is a residue having the formula:

P—X—M—R wherein P is a photophore which emits light upon exposure to such excitation means, X is a linkage which is cleavable by said enzyme, M is a modulator for said light emission of said photophore, and R is a linking group through which said label component is covalently bound to the binding component in said conjugate, said labeled conjugate and said cleaved indicator product emitting substantially different amounts of light upon exposure to said excitation means due to modulation of the emission of P by the proximity of M in said labeled conjugate.

24. The reagent means of claim 23 wherein P is a fluorescer.

25. The reagent means of claim 24 wherein said excitation means is light of a predetermined first wavelength, said fluorescer P emitting light at a second wavelength, and wherein M is a quencher which absorbs the fluorescent emission of P at said second wavelength, said labeled conjugate exhibiting substantially less fluorescence of said second wavelength than said cleaved indicator product upon exposure to light of said predetermined first wavelength due to quenching of the fluorescence of P by the proximity of M in said labeled conjugate.

26. The reagent means of claim 25 wherein quenching of the fluorescence of P by M is due essentially to direct intramolecular collision and wherein said fluorescer P comprises a residue of flavin, anthracene, tryptophan, o-aminobenzoic acid, 2-aminoethylnaphthylamine, ethenoadenosine, acridine, or indole.

27. The reagent means of claim 25 wherein quenching of the fluorescence of P by M is due essentially to resonance energy transfer and wherein said fluorescer P comprises a residue of naphthalene, tryptophan, fluorescein, thiochrome, N-[p-(2-benzoxazolyl)phenyl]-maleimide, or N-(4-dimethylamino-3,5-dinitrophenyl)-maleimide.

28. The reagent means of claim 25 wherein said label component is flavin adenine dinucleotide (FAD) coupled through the adenine moiety by the linking group R to said binding component of the labeled conjugate, the flavin portion of FAD serving as said fluorescer, the adenosine moiety of FAD serving as said quencher, and the pyrophosphate linking group in FAD serving as said enzyme cleavable linkage, and wherein said enzyme is nucleotide pyrophosphatase.

29. The reagent means of claim 28 wherein FAD is coupled at the $N^6$ position of the adenine moiety to the linking group R.

30. The reagent means of claim 25 wherein said quencher M is a fluorescer which emits light at a third wavelength.

31. The reagent means of claim 23 wherein P is a chemiluminescer and M is a quencher which absorbs the emission of P, and wherein said excitation means comprises chemical reagents which react with said chemiluminescer to cause same to emit light, said labeled conjugate emitting substantially less light than said detectable indicator product upon exposure to said chemical reagents due to quenching of the chemiluminescence of P by the proximity of M in said labeled conjugate.

32. The reagent means of claim 23 wherein said ligand is selected from the group consisting of antigens and antibodies thereto; haptens and antibodies thereto; and hormones, vitamins, metabolites, and pharmacological agents, and their receptors and binding substances.

33. In a reagent means for use in a homogeneous specific binding assay method for determining a ligand in a liquid medium, or for determining the ligand binding capacity of a liquid medium suspected to contain a specific binding partner of said ligand, which means comprises
  (1) a labeled conjugate having a label component coupled to said ligand or a binding analog thereof, which conjugate is cleavable by an enzyme to produce an indicator product which fluoresces upon excitation with light of a predetermined first wavelength, emitting light at a second wavelength,
  (2) said enzyme which cleaves said labeled conjugate, and
  (3) where said ligand is under determination, a specific binding partner of said ligand, the improvement which comprises employing as said label component of said labeled conjugate, a residue having the formula:

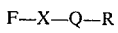

wherein F is a fluorescer which is excited by light of said predetermined first wavelength to emit light at said second wavelength, X is a linkage which is cleavable by said enzyme, Q is a quencher which when proximal to fluorescer F absorbs the fluorescent emission of fluorescer F at said second wavelength, and R is a linking group through which said label component is covalently bound to said ligand or analog thereof in said conjugate, said labeled conjugate exhibiting substantially less fluorescence at said second wavelength than said cleaved indicator product upon irradiation with light of said predetermined first wavelength due to quenching of the fluorescence of F by proximity of Q in said labeled conjugate.

34. The reagent means of claim 33 wherein quenching of the fluorescence of F by Q is due essentially to direct intramolecular collision and wherein said fluorescer F comprises a residue of flavin, anthracene, tryptophan, o-aminobenzoic acid, 2-aminoethylnaphthylamine, ethenoadenosine, acridine, or indole.

35. The reagent means of claim 33 wherein quenching of the fluorescence of F by Q is due essentially to resonance energy transfer and wherein said fluorescer F comprises a residue of naphthalene, tryptophan, fluorescein, thiochrome, N-[p-(2-benzoxazolyl)phenyl]-maleimide, or N-(4-dimethylamino-3,5-dinitrophenyl)-maleimide.

36. The reagent means of claim 33 wherein said label component is flavin adenine dinucleotide (FAD) coupled through the adenine moiety by the linking group R to said binding component of the labeled conjugate, the flavin portion of FAD serving as said fluorescer, the adenosine moiety of FAD serving as said quencher, and the pyrophosphate linking group in FAD serving as said enzyme cleavable linkage, and wherein said enzyme is nucleotide pyrophosphatase.

37. The reagent means of claim 36 wherein FAD is coupled at the $N^6$ position of the adenine moiety to the linking group R.

38. The reagent means of claim 33 wherein said ligand is selected from the group consisting of antigens and antibodies thereto; haptens and antibodies thereto; and hormones, vitamins, metabolites, and pharmacological agents, and their receptors and binding substances.

39. The reagent means of claim 33 wherein said ligand is an antigenic polypeptide or protein or a hapten having a molecular weight of at least 100.

40. The reagent means of claim 33 wherein said ligand is a hapten having a molecular weight of between 100 and 1500.

* * * * *

UNITED STATES PATENT AND TRADEMARK OFFICE
CERTIFICATE OF CORRECTION

PATENT NO. : 4,318,981

DATED : March 9, 1982

INVENTOR(S) : John F. Burd et al

It is certified that error appears in the above—identified patent and that said Letters Patent is hereby corrected as shown below:

The title page should appear as shown on the attached sheet.

Signed and Sealed this

Twenty-fifth Day of May 1982

[SEAL]

Attest:

GERALD J. MOSSINGHOFF

Attesting Officer — Commissioner of Patents and Trademarks

United States Patent [19]

Burd et al.

[11] 4,318,981

[45] Mar. 9, 1982

[54] HOMOGENEOUS SPECIFIC BINDING ASSAY EMPLOYING AN INTRAMOLECULARLY MODULATED PHOTOGENIC ENZYME SUBSTRATE LABEL

[75] Inventors: John F. Burd; Thomas M. Li, both of Elkhart, Ind.

[73] Assignee: Miles Laboratories, Inc., Elkhart, Ind.

[21] Appl. No.: 143,497

[22] Filed: Apr. 24, 1980

[51] Int. Cl.³ .............................................. C12Q 1/66
[52] U.S. Cl. .................................... 435/7; 23/230 B; 424/12
[58] Field of Search ............................. 435/7; 424/12; 23/230 B

[56] References Cited

U.S. PATENT DOCUMENTS

| | | | |
|---|---|---|---|
| 3,880,934 | 4/1975 | Rammler | 435/7 X |
| 3,996,345 | 12/1976 | Ullman et al. | 435/7 X |
| 4,134,792 | 1/1979 | Boguslaski et al. | 435/7 X |
| 4,174,384 | 11/1979 | Ullman et al. | 435/7 X |
| 4,230,797 | 10/1980 | Boguslaski et al. | 435/7 |
| 4,232,119 | 11/1980 | Carlsson et al. | 435/7 |
| 4,238,195 | 12/1980 | Boguslaski et al. | 435/7 X |

*Primary Examiner*—Robert J. Warden
*Attorney, Agent, or Firm*—Andrew L. Klawitter

[57] ABSTRACT

A homogeneous specific binding assay method and reagent means for determining a ligand, such as a hapten, antigen or antibody, in, or the ligand binding capacity of, a liquid medium employing a labeled conjugate which upon enzymatic cleavage produces a detectable indicator product. The improvement comprises employing as the label component in the labeled conjugate, a residue having the formula:

$$P-X-M-R$$

wherein P is a photophore, e.g., a fluorescer, which emits light upon exposure to excitation means, X is an enzymatically cleavable linkage, M is a modulator, e.g., a quencher, for said light emission of the photophore, and R is a linking group to the binding component, e.g., the ligand or analog thereof, in the labeled conjugate. The labeled conjugate and the cleaved indicator product emit substantially different amounts of light upon excitation due to modulation of the emission of photophore P by the proximity of modulator M in the labeled conjugate.

40 Claims, 2 Drawing Figures